United States Patent
Jagannathan et al.

(10) Patent No.: US 10,882,842 B2
(45) Date of Patent: Jan. 5, 2021

(54) PYRIDINIUM COMPOUNDS, A SYNTHESIS METHOD THEREFOR, METAL OR METAL ALLOY PLATING BATHS CONTAINING SAID PYRIDINIUM COMPOUNDS AND A METHOD FOR USE OF SAID METAL OR METAL ALLOY PLATING BATHS

(71) Applicant: Atotech Deutschland GmbH, Berlin (DE)

(72) Inventors: Rangarajan Jagannathan, Berlin (DE); James Adolf, Berlin (DE); Jun Wu, Berlin (DE); Lars Kohlmann, Berlin (DE); Heiko Brunner, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 16/483,053

(22) PCT Filed: Jan. 26, 2018

(86) PCT No.: PCT/EP2018/051926
§ 371 (c)(1),
(2) Date: Aug. 2, 2019

(87) PCT Pub. No.: WO2018/145919
PCT Pub. Date: Aug. 16, 2018

(65) Prior Publication Data
US 2020/0231565 A1 Jul. 23, 2020

(30) Foreign Application Priority Data
Feb. 9, 2017 (EP) ..................... 17155408

(51) Int. Cl.
| C07D 401/12 | (2006.01) |
| C25D 3/38 | (2006.01) |
| C25D 3/58 | (2006.01) |
| C25D 7/12 | (2006.01) |

(52) U.S. Cl.
CPC ............. *C07D 401/12* (2013.01); *C25D 3/38* (2013.01); *C25D 3/58* (2013.01); *C25D 7/123* (2013.01)

(58) Field of Classification Search
CPC .......... C07D 401/12; C25D 3/38; C25D 3/58; C25D 7/123
See application file for complete search history.

(56) References Cited

U.S. PATENT DOCUMENTS

| 4,157,388 | A | 6/1979 | Christiansen |
| 5,976,341 | A | 11/1999 | Schumacher et al. |
| 6,099,711 | A | 8/2000 | Dahms et al. |
| 8,066,864 | B2 | 11/2011 | Jimenez et al. |
| 9,322,107 | B2 | 4/2016 | Brunner et al. |
| 2004/0187731 | A1 | 9/2004 | Wang et al. |
| 2007/0041363 | A1 | 2/2007 | Ferras |
| 2009/0205969 | A1 | 8/2009 | Jimenez et al. |
| 2012/0160698 | A1 | 6/2012 | Brunner et al. |
| 2013/0098770 | A1 | 4/2013 | Niazimbetova et al. |
| 2014/0209476 | A1 | 7/2014 | Zhou et al. |
| 2015/0299883 | A1 | 10/2015 | Brunner et al. |
| 2017/0042037 | A1 | 2/2017 | Thorseth et al. |

OTHER PUBLICATIONS

PCT/EP2018/051926; PCT International Search Report and Written Opinion of the International Searching Authority dated Mar. 15, 2018.

*Primary Examiner* — Alicia L Otton
(74) *Attorney, Agent, or Firm* — Renner, Otto, Boisselle & Sklar, LLP (57) ABSTRACT

The present invention concerns pyridinium compounds, a synthesis method for their preparation, metal or metal alloy plating baths containing said pyridinium compounds and a method for use of said metal or metal alloy plating baths. The plating baths are particularly suitable for use in filling of recessed structures in the electronics and semiconductor industry including dual damascene applications.

15 Claims, 1 Drawing Sheet

PYRIDINIUM COMPOUNDS, A SYNTHESIS METHOD THEREFOR, METAL OR METAL ALLOY PLATING BATHS CONTAINING SAID PYRIDINIUM COMPOUNDS AND A METHOD FOR USE OF SAID METAL OR METAL ALLOY PLATING BATHS

The present application is a U.S. National Stage Application based on and claiming benefit and priority under 35 U.S.C. § 371 of International Application No. PCT/EP2018/051926, filed 26 Jan. 2018, which in turn claims benefit of and priority to European Application No. 17155408.2 filed 9 Feb. 2017, the entirety of both of which is hereby incorporated herein by reference.

FIELD OF THE INVENTION

The present invention concerns pyridinium compounds, a synthesis method for their preparation, metal or metal alloy plating baths containing said pyridinium compounds and a method for use of said metal or metal alloy plating baths.

The plating baths are particularly suitable for filling of recessed structures in the electronics and semiconductor industry including dual damascene applications.

BACKGROUND OF THE INVENTION

The wet-chemical deposition of metals and metal alloys (metal plating) is widely used in various industries for the manufacturing of decorative and functional coatings. A large number of metals and metal alloys can thus be formed on various substrates. Of particular interest in the electronics and semiconductor industry is copper plating. Copper is used in these industries for its high conductivity and relatively low price. Copper is used to build up the conductive lines, often by electrolytic copper deposition as this is fast and cost-efficient.

Plating baths for electrolytic deposition of copper are inter alia used for manufacturing printed circuit boards and IC substrates where fine structures like trenches, through holes (TH), blind micro vias (BMV) and pillar bumps need to be filled or build up with copper. Another application of such electrolytic deposition of copper is filling of recessed structures such as through silicon vias (TSV) and dual damascene plating or forming redistribution layers (RDL) and pillar bumps in and on semiconducting substrates. Still another application which is becoming more demanding is filling through glass vias, i.e. holes and related recessed structures in glass substrates with copper or copper alloys by electroplating.

Conventionally, a combination of various additives is used in such plating bath compositions. For example, electrolytic copper plating baths comprise a multitude of individual additives including levelers, carrier-suppressors and accelerator-brighteners.

The patent application EP 1 069 211 A2 discloses aqueous copper plating baths comprising a source of copper ions, an acid, a carrier additive, a brightener additive and a leveler additive which can be poly[bis(2-chloroethyl)ether-alt-1,3-bis[3-(dimethylamino)propy]urea (CAS-No. 68555-36-2) which contains an organo-bound halide atom (e.g., covalent C-CL bonds) in at least one terminus.

US 2009/0205969 A1 describes cross-linked polymers made from urea, N,N-dialkylaminoalkylamine and N,N-bis-(aminoalkyl)-alkylamine as additive for electrolytic metal deposition. The process disclosed therein relates to electrolytic zinc deposition.

Similar urea-based polymers are also reported in U.S. Pat. No. 4,157,388 wherein all urea moieties are bridged via nitrogen containing alkylenes, i.e. secondary, tertiary amines and the like. Cationic derivatives and their use in electrolytic plating bath are disclosed in the German patent application DE 10 2005 060 030 A1. The individual urea moieties in these polymers are linked by quarternary ammonium derivatives.

Also, WO 2007/024606 teaches urea, thiourea and polymers as additives in cosmetic applications wherein the individual urea, thiourea and moieties are linked by quarternary ammonium moieties.

Ureyl polymers are known in the art from EP 2 735 627 A1 as levelers for the electrolytic deposition of copper. Such polymers are can be obtained by a polyaddition of aminourea derivatives and nucleophiles. WO 2011/029781 teaches the same polymers for the electrolytic deposition of zinc.

However, such additives when used in acidic copper plating baths are not suitable to fulfil the current and future requirements in manufacture of advanced printed circuit boards, IC substrates and metallization of semiconducting and glass substrates. Depending on the circuitry layout, BMVs' in printed circuit boards and IC substrates need to be filled with copper not only conformally but completely. Typical requirements for BMV filling are for example: obtaining a completely filled BMV while depositing no more than 12 to 18 μm of copper onto the neighboring planar substrate areas and at the same time creating a dimple on the outer surface of the filled BMV of no more than 5 μm.

In metallization of semiconducting wafers, TSV filling must lead to a complete and void-free filling with copper while creating no more than ⅓ of via diameter of overplated copper onto the neighboring planar areas. Similar requirements are demanded for filling through glass vias with copper.

OBJECTIVE OF THE PRESENT INVENTION

Thus, it is an objective of the present invention to provide a compound usable in metal plating baths, preferably in a copper plating bath for electrolytic deposition of copper or copper alloys, which fulfils the requirements for above mentioned applications in the field of printed circuit board and IC substrate manufacturing as well as metallization of semiconducting substrates like TSV filling, dual damascene plating, deposition of redistribution layers or pillar bumping and filling of through glass vias and blind micro vias (BMV).

SUMMARY OF THE INVENTION

Above objectives are solved by a compound comprising a building block according to formula (I)

(I)

wherein each A represents a unit independently selected from the following formulae (A1) and (A2)

-continued (A2)

wherein
$R^{a1}$, $R^{a2}$, $R^{a3}$ and $R^{a5}$ are each selected independently from the group consisting of C1-C12-alkanediyl and —$(CH_2)_c$—[$CH(R^{a6})$]—$CH_2$—$O]_d$—$(CH_2)_e$— wherein c is an integer ranging from 0 to 3; d is an integer ranging from 1 to 100; e is an integer ranging from 1 to 3; each $R^{a6}$ is independently from each other selected from the group consisting of hydrogen, alkyl, aryl and aralkyl; each $R^a$ is independently selected from the group consisting of alkanediyl, arenediyl and —$(CH_2)_f$—[$CH(R^{a7})$]—$CH_2$—$O]_g$—$(CH_2)_h$—, wherein f is an integer ranging from 0 to 3; g is an integer ranging from 1 to 100; h is an integer ranging from 1 to 3; each $R^{a7}$ is independently from each other selected from the group consisting of hydrogen, alkyl, aryl and aralkyl;
each $X^1$ and $X^2$ are independently selected from the group consisting of wherein Z is selected from —$CH_2$—, O, S; z and z' are integers independently ranging from 1 to 6, each $R^{a8}$ and $R^{a9}$ are independently selected from the group consisting of hydrogen, alkyl, aryl, aralkyl and —$CH_2$—$CH_2$—$(OCH_2CH_2)_y$—OH wherein y is an integer from 1 to 4; each $Y^1$, $Y^2$ and $Y^3$ are independently selected from the group consisting of O and $N(R^{a10})$ wherein each $R^{a10}$ is independently selected from the group consisting of hydrogen, alkyl, aryl and aralkyl;
a is an integer ranging from 1 to 40; and
each D is independently selected from the group consisting of —$CH_2$—$CH(OH)$—$CH_2$—, —$CH_2$—$CH(SH)$—$CH_2$—, —$(CH_2)_i$—[$CH(R^{d1})$]—$CH_2$—$O]_j$—$(CH_2)_k$— and —$CH_2$—$CH(OH)$—$(CH_2)_l$—[$CH(R^{d2})$]—$CH_2$—$O]_m$—$(CH_2)_n$—$CH(OH)$—$CH_2$— wherein i is an integer ranging from 0 to 3; j is an integer ranging from 1 to 100; k is an integer ranging from 1 to 3; each $R^{d1}$ is independently from each other selected from the group consisting of hydrogen, alkyl, aryl and aralkyl; l is an integer ranging from 1 to 3; m is an integer ranging from 1 to 100; n is an integer ranging from 1 to 3; each $R^{d2}$ is independently from each other selected from the group consisting of hydrogen, alkyl, aryl and aralkyl.

The compounds comprising a building block according to formula (I) are referred to in this specification as "pyridinium compounds".

Above objectives are also solved by the use of at least one pyridinium compound in a metal or metal alloy plating bath, preferably (by their use) in a copper or copper alloy plating bath. The metal or metal alloy plating bath is suitable to deposit a metal or a metal alloy, preferably copper or a copper alloy, on at least one surface of a substrate.

Further, above objectives are solved by a metal or metal alloy plating bath comprising at least one type of reducible metal ions characterized in that said plating bath comprises at least one such pyridinium compound.

Above objectives are further solved by a method for deposition of metal or metal alloy onto at least one surface of a substrate comprising the steps
(i) providing a substrate,
(ii) contacting the surface of the substrate with an aqueous metal or metal alloy plating bath according to the invention, and
(iii) optionally, applying an electrical current between the substrate and at least one anode,
and thereby depositing a metal or metal alloy on at least a portion of the surface of a substrate.

It is an advantage of the present invention that very smooth and even metal or metal alloy deposits, preferably copper deposits, can be formed without any (substantial) overburden or dimple (see Application Example 1).

It is an advantage of the present invention that the inventive pyridinium compound used in a copper plating bath allows for copper deposits with very few organic impurities therein to be formed (see Application Example 4). This is particularly desired for semiconductor applications so as this gives rise to bigger copper grains with less voids which in turn results in better conductivity of the copper deposits. Organic impurities can for example be incorporated into the copper deposit from organic or polymeric additives used in the copper plating bath such as levelers, solvents, surfactants/wetting agents, brighteners and carriers. Typically, they are found as organic or polymeric compounds comprising the elements carbon, hydrogen, halides, sulfur and oxygen.

It is a further advantage of the present invention that copper deposits with very few defects (such as SP2 and SP3 defects) can be obtained (see Application Example 3 and Comparative Application Example 1). This is required by the semiconductor industry as high defect counts can decrease final product yield.

It is yet a further advantage of the present invention that uniformal and complete filling of recessed structures with copper can be obtained. It is also advantageous that the copper deposits are free of voids (see Application Example 2).

It is another advantage of the present invention that in the preparation of the pyridinium compounds very few side reactions can occur, giving rise to a reliable and easy synthesis with reproducible results.

DETAILED DESCRIPTION OF THE INVENTION

Percentages throughout this specification are weight-percentages (wt.-%) unless stated otherwise. Yields are given as percentage of the theoretical yield. Concentrations given in this specification refer to the volume or mass of the entire solutions unless stated otherwise. The terms "deposition" and "plating" are used interchangeably herein. Also, "layer" and "deposit" are interchangeably in this specification.

The term "alkyl" according to the present invention comprises branched or unbranched alkyl groups comprising cyclic and/or non-cyclic structural elements, wherein cyclic structural elements of the alkyl groups naturally require at least three carbon atoms. C1-CX-alkyl in this specification and in the claims refers to alkyl groups having 1 to X carbon atoms (X being an integer). C1-C8-alkyl for example includes, among others, methyl, ethyl, n-propyl, iso-propyl, n-butyl, isobutyl, sec-butyl, tert-butyl, n-pentyl, iso-pentyl, sec-pentyl, tert-pentyl, neo-pentyl, hexyl, heptyl and octyl. Substituted alkyl groups may theoretically be obtained by replacing at least one hydrogen by a functional group. Unless stated otherwise, alkyl groups are preferably selected from substituted or unsubstituted C1-C8-alkyl, more preferably from substituted or unsubstituted so C1-C4-alkyl because of their improved water-solubility. The "alkenyl" is an unsaturated alkyl group comprising at least one olefinic (C=C-double) bond. Above-described preferences for the alkyl groups apply for alkenyl groups mutatis mutandis.

The term "alkanediyl" is the corresponding group having two free valences (bonding sites). Sometimes, it is referred to as "alkylene" in the art. Said residues according to the present invention comprise cyclic and/or non-cyclic structural elements and can be linear and/or branched. C1-C4-alkanediyl for example includes, among others, methane-1,1-diyl, ethane-1,2-diyl, ethane-, 1-diyl, propane-1,3-diyl, propane-1,2-diyl, propane-1,1-diyl, butane-1,4-diyl, butane-1,3-diyl, butane-1,2-diyl, butane-1,1-diyl, butane-2,3-diyl. Furthermore, individual hydrogen atoms bound to the alkanediyl compound may in each case be substituted by a functional group such as those defined above for the alkyl group. Unless stated otherwise, alkanediyl groups are preferably selected from substituted or unsubstituted C1-C8-alkanediyl, more preferably from substituted or unsubstituted C1-C4-alkanediyl because of their improved water-solubility.

The term "aryl" according to the invention refers to ring-shaped aromatic hydrocarbon residues, for example phenyl or naphtyl where individual ring carbon atoms can be replaced by N, O and/or S, for example benzothiazolyl. Preferably, no carbon atoms are substituted to avoid undesired side-reactions in the preparation of the pyridinium compounds. Furthermore, aryl groups are optionally substituted by replacing a hydrogen atom in each case by a functional group. The term C5-CX-aryl refers to aryl groups having 5 to X carbon atoms (optionally replaced by N, O and/or S) in the ring-shaped aromatic group (X naturally being an integer). C5-C6-aryl is preferred unless stated otherwise. "Arenediyl" is the divalent corresponding group to aryl, e.g. phenylene. Above-described preferences for the aryl groups apply for arenediyl groups mutatis mutandis.

The term "alkaryl" according to the invention refers to hydrocarbon groups comprising at least one aryl and at least one alkyl group such as benzyl and p-tolyl. The bonding of such an alkaryl group to other moieties may occur via the alkyl or the aryl group of the alkaryl group. Above-described preferences for the alkyl and aryl groups apply for alkaryl groups mutatis mutandis.

Unless stated otherwise, above-described groups are substituted or unsubstituted. Functional groups as substituents are preferably selected from the group consisting of hydroxyl (—OH) and carboxyl (—CO$_2$H) to improve the water-solubility of the treatment additives.

If more than one residue is to be selected from a given group, each of the residues is selected independently from each other unless stated otherwise hereinafter, meaning they can be selected to be the same members or different members of said group. The bonding sites in some chemical formulae are emphasized by a wavy line ("〰〰") as is customary in the art.

The Pyridinium Compounds

Preferably, each $R^{a1}$, $R^{a2}$, $R^{a3}$ and $R^{a5}$ are independently selected from C1-C8-alkanediyl and —(CH$_2$)$_c$—[CH(R$^{a6}$)—CH$_2$—O]$_d$—(CH$_2$)$_e$— wherein c is an integer ranging from 2 to 3; d is an integer ranging from 1 to 20; e is an integer ranging from 2 to 3; each $R^{a6}$ is independently from each other selected from the group consisting of hydrogen, alkyl, aryl and aralkyl. More preferably, each $R^{a1}$, $R^{a2}$, $R^{a3}$ and $R^{a5}$ are independently selected from C1-C4-alkanediyl and —(CH$_2$)$_c$—[CH(R$^{a6}$)—CH$_2$—O]$_d$—(CH$_2$)$_e$— wherein c is an integer ranging from 2 to 3; d is an integer ranging from 1 to 20; e is an integer ranging from 2 to 3; each $R^{a6}$ is independently from each other selected from the group consisting of hydrogen, C1-C4-alkyl and phenyl. Even more preferably, each $R^{a1}$, $R^{a2}$, $R^{a3}$ and $R^{a5}$ are independently selected from 1,1-methylene (—CH$_2$—), 1,2-ethylene (—CH$_2$—CH$_2$—), 1,3-propylene (—CH$_2$—CH$_2$—CH$_2$—), —(CH$_2$)$_2$—O—(CH$_2$)$_2$— and —(CH$_2$)$_2$—O—(CH$_2$)$_2$—O—(CH$_2$)$_2$— to improve the solubility of the pyridinium compounds. Most preferably, $R^{a1}$, $R^{a2}$, $R^{a3}$ and $R^{a5}$ are 1,1-methylene (—CH$_2$—) to further facilitate the synthesis of the pyridinium compounds.

Preferably, each $R^{a4}$ is independently selected from the group consisting of C1-C8-alkanediyl, arenediyl and —(CH$_2$)$_f$—[CH(R$^{a7}$)—CH$_2$—O]$_g$—(CH$_2$)$_h$—, wherein f is an integer ranging from 0 to 3; g is an integer ranging from 1 to 20; h is an integer ranging from 1 to 3; each $R^{a7}$ is independently from each other selected from the group consisting of hydrogen, C1-C8-alkyl, aryl and aralkyl. More preferably, each $R^{a4}$ is independently selected from 1,2-ethylene (—CH$_2$—CH$_2$—), 1,3-propylene (—CH$_2$—CH$_2$—CH$_2$—), —(CH$_2$)$_2$—O—(CH$_2$)$_2$—, —(CH$_2$)$_2$—O—(CH$_2$)$_2$—O—(CH$_2$)$_2$— and —(CH$_2$)$_2$—O—(CH$_2$)$_2$—O—(CH$_2$)$_2$—O—(CH$_2$)$_2$—.

Preferably, $R^{a1}$ to $R^{a5}$ are free of nitrogen atoms such as amino groups. This avoids undesired side reactions of nucleophiles used to synthesize the pyridinium compounds. The same applies to $R^{a6}$ if comprised in the pyridinium compounds.

If Z is contained in the pyridinium compounds, it is preferably selected from the group consisting of —CH$_2$— and O to avoid undesired side-reactions while preparing the pyridinium compounds. The integers z and z' preferably range from 1 to 3, more preferably with the proviso that the sum of z and z' ranges from 2 to 4. Even more preferably, the integers z and z' are 1 to 2 while the sum of z and z' equals 2 or 3.

If $R^{a8}$ and $R^{a9}$ are contained in the pyridinium compounds, they are preferably selected from the group consisting of C1-C8-alkyl and —CH$_2$—CH$_2$—(OCH$_2$CH$_2$)$_y$—OH wherein y is an integer from 1 to 4, more preferably they are selected from C1-C4-alkyl.

Preferably, each $Y^1$, $Y^2$ and $Y^1$ are independently selected from the group consisting of O and N(R$^{a10}$) wherein each $R^{a10}$ is independently selected from the group consisting of C1-C4-alkyl. More preferably $Y^1$, $Y^2$ and $Y^3$ are O (oxygen), thus forming urea moieties. This is preferred due to the avoidance of side-reactions when preparing the pyridinium compounds (no further nucleophilic center).

Preferably, $X^1$ and $X^2$ are

This facilitates inter alia the synthesis of the pyridinium compounds.

The pyridinium compounds comprise one or more pyridyl moieties:

$R^{a1}$, $R^{a2}$, $R^{a3}$ and $R^{a5}$ may be bound to said pyridyl moieties in ortho-, meta- or par-position of the latter (with respect to the nitrogen atom comprised by the pyridine ring). Preferably, each of the bonding occurs in meta- or para-position (with respect to the nitrogen atom comprised by the pyridine ring), more preferably all bonds of $R^{a1}$, $R^{a2}$, $R^{a3}$ and $R^{a5}$ are in para-position (with respect to the nitrogen atom comprised by the pyridine ring). These outlined preferences are due to enhanced levelling properties of the respective pyridinium compounds in copper plating baths (see Application Example 1).

The Integer a preferably ranges from 2 to 20, more preferably from 3 to 15 and even more preferably from 4 to 13. These outlined preferences are due to enhanced levelling properties of the respective pyridinium compounds in copper plating baths (see Application Example 1).

Preferably, at least one A is selected to be a unit represented by formula (A1). More preferably, all A are selected to be units represented by formula (A1).

Preferably, at least one A is selected to be a unit represented by formula (A1-1) or (A1-2)

Then, $Y^1$ is preferably selected to be O forming exclusively urea moieties and more preferably, $R^{a1}$ and $R^{a2}$ are methylene (—$CH_2$—) for the ease of synthesis.

More preferably, all A are selected to be a unit represented by formula (A1-1) or (A1-2)

Even more preferably, $Y^1$ is preferably selected to be O forming exclusively urea moieties. Even more preferably, $R^{a1}$ and $R^{a2}$ are methylene (—$CH_2$—) for the ease of synthesis. These outlined preferences are among others due to enhanced levelling properties of the respective pyridinium compounds in copper plating baths (see Application Example 1).

In a more preferred embodiment of the present invention, at least one A is, even more preferred all A are, selected to be one or more units represented by formula (A1-1)

In this embodiment $Y^1$ is preferably selected to be 0 forming exclusively urea moieties. Even more preferably, $R^{a1}$ and $R^{a2}$ are methylene (—$CH_2$—) for the ease of synthesis. These outlined preferences are among others due to enhanced levelling properties of the respective pyridinium compounds in copper plating baths (see Application Example 1).

Preferably, each D is independently selected from the group consisting of
—$CH_2$—$CH(OH)$—$CH_2$—, —$(CH_2)_i$—$[CH(R^{d1})$—$CH_2$—$O]_j$—$(CH_2)_k$— and —$CH_2$—$CH(OH)$—$(CH_2)_l$—$[CH(R^{d2})$—$CH_2$—$O]_m$—$(CH_2)_n$—$CH(OH)$—$CH_2$—
wherein i is an integer ranging from 0 to 3; J is an integer ranging from 1 to 100; k is an integer ranging from 1 to 3; each $R^{d1}$ is independently from each other selected from the group consisting of hydrogen, alkyl, aryl and aralkyl, more preferably it is selected from hydrogen, C1-C4-alkyl and phenyl, even more preferably from hydrogen and C1-C4-alkyl, yet even more preferably from hydrogen and methyl; l is an integer ranging from 1 to 3; m is an integer ranging from 1 to 100; n is an integer ranging from 1 to 3; each $R^{d2}$ is independently from each other selected from the group consisting of hydrogen, alkyl, aryl and aralkyl, more preferably it is selected from hydrogen, C1-C4-alkyl and phenyl, even more preferably from hydrogen and C1-C4-alkyl, yet even more preferably from hydrogen and methyl.

More preferably, each D is —(CH$_2$)$_i$—[CH(R$^{d1}$)—CH$_2$—O]$_j$—(CH$_2$)$_k$— wherein each i is 2 or 3; each j is an integer ranging from 1 to 20 or 25, each k is an integer ranging from 2 to 3 and each R$^{d1}$ is independently selected from the group consisting of hydrogen and C1-C4-alkyl, even more preferably it is selected from hydrogen and methyl.

In an even more preferred embodiment, D selected from the group consisting of —CH$_2$—CH$_2$—O—CH$_2$—CH$_2$—, —CH$_2$—CH$_2$O—CH$_2$—CH$_2$—O—CH$_2$—CH$_2$— and —CH$_2$—CH$_2$—O—CH$_2$—CH$_2$—O—CH$_2$—CH$_2$—O—CH$_2$—CH$_2$—.

The weight average molecular mass M$_w$ of the pyridinium compound preferably ranges from 250 to 10000 g/mol, more preferably from 350 to 7500 g/mol and even more preferably from 500 to 6000 g/mol, yet even more preferably from 1500 to 5000 g/mol. These outlined preferences are due to enhanced levelling properties in copper plating baths of the respective pyridinium compounds (see Application Example 1).

If any (terminal) tertiary amino groups (including nitrogen atoms bound in a pyridine ring) are present in the pyridinium compounds, they are optionally converted into the respective quaternary ammonium group in accordance with the desired properties by using an organic monohalide or organic monopseudohalides such as benzyl chloride, alkyl chloride like 1-chlorohexane or allyl chloride or their corresponding bromides and mesylates, or by using an appropriate mineral acid, such as hydrochloric acid, hydrobromic acid, hydroiodic acid or sulfuric acid.

The pyridinium compounds preferably do not contain any organically bound halogen, such as a covalently bound C—Cl moiety.

Synthesis of the Pyridinium Compounds

The present invention further concerns a method of synthesizing the pyridinium compounds. At least one starting material represented by one of the following formulae (M1) and M2)

(M1)

(M2)

wherein
R$^{m1}$, R$^{m2}$, R$^{m3}$ and R$^{m5}$ are each selected independently from the group consisting of C1-C12-alkanediyl and —(CH$_2$)$_\alpha$—[CH(R$^{m6}$)—CH$_2$—O]$_\beta$—(CH$_2$)$_\chi$— wherein α is an integer ranging from 0 to 3; β is an integer ranging from 1 to 100; χ is an integer ranging from 1 to 3; each R$^{m6}$ is independently from each other selected from the group consisting of hydrogen, alkyl, aryl and aralkyl;
each R$^{m4}$ is independently selected from the group consisting of alkanediyl, arenediyl and —(CH$_2$)$_\delta$—[CH(R$^{m7}$)—CH$_2$—O]$_\varepsilon$—(CH$_2$)$_\phi$—, wherein δ is an integer ranging from 0 to 3; ε is an integer ranging from 1 to 100; φ is an integer ranging from 1 to 3; each R$^{m7}$ is independently from each other selected from the group consisting of hydrogen, alkyl, aryl and aralkyl;

each of M$^1$, M$^3$ and M$^4$ is independently selected from the group consisting of 0 and N(R$^{m10}$) wherein each R$^{m10}$ is independently selected from the group consisting of hydrogen, alkyl, aryl and aralkyl; and each of M$^2$ and M$^5$ is independently selected from the group consisting of wherein Z is selected from —CH$_2$—, O, S; ζ and ζ' are integers independently ranging from 1 to 6, each R$^{m8}$ and R$^{m9}$ are independently selected from the group consisting of hydrogen, alkyl, aryl, aralkyl and —CH$_2$—CH$_2$—(OCH$_2$CH$_2$)$_\psi$—OH wherein ψ is an integer from 1 to 4 is reacted with one or more of the following compounds (B1) to (B4)

(B1)

(B2)

(B3)

(B4)

wherein
each LG is independently selected from the group consisting of triflate, nonaflate, alkyls sulfonates, arylsulfonates and halides;

ι is an integer ranging from 0 to 3; φ is an integer ranging from 1 to 100; κ is an integer ranging from 1 to 3; each R$^{n1}$ is independently from each other selected from the group consisting of hydrogen, alkyl, aryl and aralkyl; λ is an integer ranging from 1 to 3; μ is an integer ranging from 1 to 100; ν is an integer ranging from 1 to 3; each R$^{n2}$ is independently from each other selected from the group consisting of hydrogen, alkyl, aryl and aralkyl.

As the starting materials represented by formulae (M1) and (M2) form the units represented by formulae (A1) and (A2), respectively, above described preferred embodiments for the pyridinium compounds naturally apply mutatis mutandis for the starting materials. This means for example that the preferred embodiments described hereinbefore for A1 correspond to those of M1 and so forth. The same applies mutatis mutandis for the compounds (B1) to (B4) which form the units D of the pyridinium compounds.

The reaction of the one or more starting materials represented by formula (M1) and (M2) and the one or more compounds (B1) to (B4) is typically carried out in a solvent, preferably in a polar solvent. Suitable solvents are water, glycols, acetonitrile and alcohols or mixtures thereof, water being preferred for its ecologically benign character. The reaction temperature usually ranges from 50 to 100° C., preferably from 60 to 90° C., more preferably from 75 to 85° C. The reaction is preferably continued until all of the starting materials are consumed which can for example be detected by pH measurements using a pH sensor since the pH decreases due to the conversion of basic nitrogen atoms in the pyridine rings to the respective quaternary ammonium moieties. Once the pH value becomes constant for a certain period of time, e.g. at least 10 min, the reaction is complete and can be terminated. Alternatively, the reaction is carried out for a time of 1 to 120 h, preferably for 12 to 100 h, more preferably for 24 to 84 h.

In a preferred embodiment of the invention, the molar ratio $$\frac{n_{(M_1+M_2)}}{n_{(B_1+B_2+B_3+B_4)}}$$

of the amount of substance of starting materials according to formula (M1) and (M2) (which means in this connection the overall amount of substance of all starting materials according to formula (M1) and (M2) if more than one is used) to the amount of substance of compounds (B1) to (B4) (which means in this connection the overall amount of substance of all compounds (B1) to (B4) if more than one is used) which is employed for the preparation of the pyridinium compound ranges from 1:1 to 1.5:1, more preferably it ranges from 1.04:1 to 1.4:1, even more preferably, it ranges from 1.05:1 to 1.25:1. This means that the molar ratio of A and D in the building block according to formula (I) lies preferably lies also said ranges, i.e. preferably 1:1 to 1.5:1, more preferably it ranges from 1.04:1 to 1.4:1, even more preferably, it ranges from 1.05:1 to 1.25:1.

The starting materials according to formula (M1) can be prepared by reacting a suitable pyridine alkylene nucleophile and urea and/or guanidine (suitably N-protected if necessary). Similarly, starting materials according to formula (M2) can be obtained by the same reaction albeit after linkage of two molecules of urea and/or guanidine (suitably N-protected if necessary) with a suitable dinucleophile (e.g. an α,ω-dichloropolyether). Use of common protection groups to mask one of the nitrogen atoms of urea and/or guanidine (two in this case) may be advisable to avoid undesired side reactions, in particular in case of guanidine. Therefore, the reaction with urea is preferred as it is easier compared to that with guanidine because protection groups are not required to avoid side-reactions.

The pyridinium compounds may be used as received or purified by conventional purification methods such as chromatography, precipitation or distillation depending on the physical properties of the pyridinium compounds. The person skilled in the art can determine suitable methods by routine experiments.

The linkages between starting materials according to formulae (M1) and/or (M2) and compounds (B1) to (B4) occur via one of the nitrogen atoms of the pyridine moiety in the starting materials according to formulae (M1) and/or (M2) and/or if present one of the nitrogen atoms in $M^2$ and $M^5$. Preferably, the linkage takes place at the nitrogen atoms of the pyridine moiety.

In another embodiment of the present invention, halide ions serving as the counter-ions of the positively charged pyridinium compounds according to the invention are replaced after preparation of the pyridinium compounds by anions such as hydroxide, sulfate, hydrogensulfate, carbonate, hydrogencarbonate, alkylsulfonate such as methane sulfonate, alkarylsulfonate, arylsulfonate, alkylcarboxylate, alkarylcarboxylate, arylcarboxylate, phosphate, hydrogenphosphate, dihydrogenphosphate, and phosphonate. The halide ions can be for example replaced by ion-exchange over a suitable ion-exchange resin. The most suitable ion-exchange resins are basic ion-exchange resins such as Amberlyst® A21. Halide ions can then be replaced by adding an inorganic acid and/or an organic acid containing the desired anions to the ion exchange resin. The enrichment of halide ions in a plating bath during use can be avoided if the pyridinium compounds contain anions other than halide ions.

In one embodiment of the present invention, the pyridinium compound comprises a building block according to the following formulae (IIa) or (IIb) or the compound is represented by the following formula (IIc)

(IIa)

(IIb)

(IIc)

wherein the pyridinium compound contains one or two terminal groups CG1 and/or CG2, which are bound to the building block and wherein the terminal group CG1, which is bound to the unit A, is selected from the group consisting of hydrogen, alkyl, aralkyl, $G^1$-, $G^2$-D-, wherein each $G^1$ is independently represented by the following formula $R^{p1}$—$(CH_2)_r$—$[CH(R^{p2})$—$CH_2$—$O]_s$—$(CH_2)_t$— with each $R^{p1}$ being selected from the group consisting of C1-C8-alkyl, C1-C8-alkenyl, aralkyl, aryl, triflate, nonaflate, alkylsulfonates, arylsulfonates and halides, r being an integer ranging from 0 to 3; s being an integer ranging from 1 to 100; t being an integer ranging from 1 to 3 and each $R^{p2}$ being independently from each other selected from the group consisting of hydrogen, alkyl, aryl and aralkyl, G² is a unit represented by one of the formulae (M1) and M2);
and wherein
the second terminal group CG2, which is bound to D, is selected from the group consisting of
hydrogen, hydroxyl group (—OH), a unit represented by formula (M1) or (M2), E, C1-C8-alkyl, aralkyl, aryl, wherein E is selected from triflate, nonaflate, alkylsulfonates, arylsulfonates and halides.

E is preferably selected from triflate, nonaflate, alkylsulfonates and arylsulfonates.

$R^{p1}$ is preferably selected from the group consisting of C1-C8-alkyl, C1-C8-alkenyl, aralkyl and aryl.

It is preferred that the pyridinium compound is represented by formula (IIc).

CG1 is preferably selected from C1-C4-alkyl, benzyl, G²-D-, $R^{p1}$—[CH($R^{p2}$)—CH$_2$—O]$_s$—(CH$_2$)$_t$— wherein s is an integer ranging from 1 to 20 (more preferably 1 to 3); t is an integer selected from 2 and 3; each $R^{p2}$ is independently from each other selected from the group consisting of hydrogen, C1-C4-alkyl and phenyl (more preferred hydrogen and methyl, most preferred hydrogen) and wherein each $R^{p1}$ is independently selected from the group consisting of C1-C4-alkyl (more preferred methyl to improve the water-solubility of the pyridinium compound). Particularly, CG1 is selected to be G²-D- to facilitate the synthesis of the pyridinium compounds.

Preferably, CG2 is a unit represented by formula (M1) or (M2).

Metal Plating Bath

The present invention further concerns metal or metal alloy plating baths comprising at least one type of reducible metal ions and at least one pyridinium compound (hereinafter referred to as "plating bath").

Reducible metal ions are understood in the context of the present invention as those metal ions which can be deposited to form a metallic layer or a metal alloy layer (under the given conditions). In the context of the present invention, reducible metal ions are preferably selected from the group consisting of gold ions, tin ions, silver ions, zinc ions, nickel ions, cobalt ions, palladium ions and copper ions. Suitable sources of said ions are water-soluble salts and/or water-soluble complexes of said metals. Non-reducible metal ions include inter alia alkaline and earth alkaline metal ions which cannot be reduced under the conditions typically applied.

If only one type of reducible metal ions is present in the plating bath according to the invention only this metal will be deposited when using the plating bath. If two or more types of reducible metal ions are present therein an alloy will be deposited. It is also possible within the means of the present invention to deposit an alloy when using certain reducing agents which will form phosphorus or boron based co-deposits such as hypophosphite or aminoboranes with one or more type of reducible metal ions. The plating baths according to the invention are suitable for depositing metals or metal alloys which can be used in the electronics and semiconductor industry.

It is possible that two or more pyridinium compounds are used as a mixture in a plating bath.

The plating bath according to the invention is an aqueous solution. The term "aqueous solution" means that the prevailing liquid medium, which is the solvent in the solution, is water. Further liquids, that are miscible with water, as for example alcohols and other polar organic liquids may be added.

Other components may be added to the plating bath such as pH adjustors (acids, bases, buffers), complexing agents (also referred to as chelating agents), stabilizing agents, reducing agents, wetting agents and the like. These components and suitable concentration thereof are known in the art.

The plating bath according to the invention may be prepared by dissolving all components in aqueous liquid medium, preferably in water.

Copper Plating Bath

In a preferred embodiment of the present invention, the at least one type of reducible metal ions are copper ions. Such a plating bath will be herein referred to as "copper plating bath". Said copper plating bath is particularly suitable for electroplating of copper; it is thus preferably an electrolytic copper plating bath. Typically, the inventive copper plating bath is suitable for filling of recessed structures and dual damascene applications.

More preferably, 99 weight percent or more of all reducible metal ions in the inventive copper plating bath ions are copper ions. Even more preferably, the inventive copper plating bath is free of further reducible metal ions other than copper ions (disregarding traces of impurities commonly present in technical raw materials and typically employed redox couples such as $Fe^{3+}/Fe^{2+}$, i.e. less than 0.1 wt.-% of such further reducible metal ions in relation to the copper ions). Particularly, the copper plating bath is free of intentionally added zinc ions. Co-deposition of zinc and copper reduces the electrical conductivity of the formed deposits significantly compared to pure copper rendering such co-deposit of zinc and copper unsuitable for the use in the electronics industry. Further, it is preferably free of tin ions for the same reasons outlined for zinc ions.

The pyridinium compound according to the invention acts as leveler in the inventive copper plating bath. The leveling function and the term "leveler" means the following: Using the copper plating bath according to the invention and the method according to the invention, it is possible to deposit copper in a very uniform manner in the structures that are to be filled, such as recessions and depressions. In particular, it is possible to fill recessions and depressions totally, reduce a deposition of copper on the surface compared to deposition in the depressions/recessions, and to avoid or at least minimize any voids or dimples. This guarantees that an extensively smooth, even copper surface is formed that exhibits practically no deformations.

The concentration of the at least one pyridinium compound according to the invention in the inventive copper plating bath preferably ranges from 0.01 mg/L to 1000 mg/L, more preferably from 0.1 mg/L to 100 mg/L and even more preferably from 0.5 mg/L to 50 mg/L and yet even more preferably from 0.8 or 5 mg/L to 20 mg/L. If more than one pyridinium compound is used, the overall concentration of all pyridinium compounds used is preferably in above-defined ranges.

Copper ions are preferably included in the bath by using one or more of the following copper ion sources: copper sulfate, copper alkyl sulfonates such as copper methane sulfonate, copper arylsulfonates such as copper p-toluene sulfonate and copper phenyl sulfonate, copper halides such as copper chloride, copper acetate, copper citrate, copper fluoroborate, copper oxide, copper carbonate and mixtures of the aforementioned. More preferably, copper sulfate, copper alkylsulfonates or mixtures of the aforementioned are used as the copper ion source. The copper ion concentration in the copper plating bath preferably ranges from 1 g/L to 70 g/L.

The copper plating bath further contains at least one acid which is preferably selected from the group consisting of sulfuric acid, fluoroboric acid, phosphoric acid and methane sulfonic acid and mixtures of the aforementioned. Said acid is preferably contained in the copper plating bath in a concentration of 1 g/L to 400 g/L, more preferably from 5 g/L to 250 g/L.

The copper plating bath preferably has a pH value of ≤3, more preferably ≤2, even more preferably of ≤1.5.

The copper plating bath optionally contains at least one accelerator-brightener additive which is known in the art. Said accelerator-brightener is preferably selected from the group consisting of organic thiol-, sulfide-, disulfide- and polysulfide-compounds. More preferred accelerator-brightener additives are selected from the group consisting of 3-(benzthiazolyl-2-thio)propylsulfonic-acid, 3-mercaptopropan-1-sulfonic acid, ethylendithiodipropylsulfonic-acid, bis-(ω-sulfophenyl)-disulfide, bis-(ω-sulfobutyl)-disulfide, bis-(ω-sulfohydroxypropyl)-disulfide, bis-(ω-sulfopropyl)-disulfide, bis-(ω-sulfopropyl)-sulfide, methyl-(ω-sulfopropyl)-disulfide, methyl(ω-sulfopropyl)-trisulfide, O-ethyl-dithiocarbonic-acid-S-(ω-sulfopropyl)-ester, thioglyco-acid, thiophosphoric-acid-O-ethyl-bis-(ω-sulfopropyl)-ester, 3-N, N-dimethylaminodithiocarbamoyl-1-propanesulfonic acid, 3,3'-thiobis(1-propanesulfonic acid), thiophosphoric-acid-tris-(ω-sulfopropyl)-ester and their corresponding salts. The concentration of all accelerator-brightener additives optionally present in the copper bath compositions preferably ranges from 0.01 mg/L to 100 mg/L, more preferably from 0.05 mg/L to 50 mg/L.

The copper plating bath optionally contains at least one further carrier-suppressor additive which is known in the art. Preferably, the at least one further carrier-suppressor additive is selected from the group consisting of polyvinylalcohol, carboxymethylcellulose, polyethylenglycol, polypropyleneglycol, stearic acid polyglycolester, alkoxylated naphtoles, oleic acid polyglycolester, stearylalcoholpolyglycolether, nonylphenolpolyglycolether, octanolpolyalkyleneglycolether, octanediol-bis-(polyalkyleneglycolether), poly(ethylenglycol-ran-propylenglycol), poly(ethylenglycol)-block-poly(propytenglycol)-block-poly(ethylenglycol), and poly(propyteneglycol)-block-poly(ethylenglycol)-block-poly(propylenglycol). More preferably, the optional carrier-suppressor additive is selected from the group consisting of polyethylenglycol, polypropylenglycol, poly(ethylenglycol-ran-propylenglycol), poly(ethylenglycol)-block-poly(propyteneglycol)-block-poly(ethylenglycol) and poly(propyleneglycol)-block-poly(ethyleneglycol)-block-poly(propylenglycol). The concentration of said optional carrier-suppressor additive in the copper plating bath preferably ranges from 0.005 g/L to 20 g/L, more preferably from 0.01 g/L to 5 g/L.

Optionally, the aqueous copper plating bath contains in addition to the inventive pyridinium compound at least one further leveler additive, which is preferably selected from the group consisting of nitrogen containing organic compounds such as polyethyleneimine, alkoxylated polyethyleneimine, alkoxylated lactams and polymers thereof, diethylenetriamine and hexamethylenetetramine, polyethylenimine bearing peptides, polyethylenimine bearing amino acids, polyvinylalcohol bearing peptides, polyvinylalcohol bearing amino acids, polyalkyleneglycol bearing peptides, polyalkyleneglycol bearing amino acids, aminoalkylene bearing pyrroles and aminoalkylene bearing pyridines, organic dyes such as Janus Green B, Bismarck Brown Y and Acid Violet 7, sulfur containing amino acids such as cysteine, phenazinium salts and derivatives thereof. Suitable ureyl polymers have been disclosed in EP 2735627 A1, said polyalkyleneglycol bearing amino acids and peptides are published in EP 2113587 B9 and EP 2537962 A1 teaches suitable aminoalkylene bearing pyrroles and pyridines. The preferred further leveler additive is selected from nitrogen containing organic pyridinium compounds. Said optional leveler additive is preferably contained in the copper plating bath in amounts of 0.1 mg/L to 100 mg/L.

The copper plating bath optionally further contains at least one source of halide ions, preferably chloride ions, in a quantity of 20 mg/L to 200 mg/L, more preferably from 30 mg/L to 60 mg/L. Suitable sources for halide ions are for example hydrochloric acid or alkali halides such as sodium chloride.

Optionally, the copper plating bath contains at least one wetting agent. These wetting agents are also referred to as surfactants in the art. The at least one wetting agent may be selected from the group of non-ionic, cationic, anionic and/or amphoteric surfactants and is used in concentration from 0.01 to 5 wt.-%.

In one embodiment of the present invention, a redox couple, such as $Fe^{2+/3+}$ ions is contained in the copper plating bath. Such a redox couple is particularly useful, if reverse pulse plating is used in combination with inert anodes for copper deposition. Suitable processes for copper plating using a redox couple in combination with reverse pulse plating and inert anodes are for example disclosed in U.S. Pat. Nos. 5,976,341 and 6,099,711. The copper plating bath is particularly suitable for electrolytic deposition of copper.

In one embodiment of the present invention, a low concentration copper plating bath is used. Said low concentration copper plating bath comprises copper ions in a concentration of 1 to 10 g/L, preferably of 2 to 8 g/L, and an acid in a concentration of 2 to 15 g/L, preferably of 5 to 10 g/L. This increases the overpotential of said bath, making deposition easier to control allowing thus for a more reproducible fill of recessed structures.

In another embodiment of the present invention, a high concentration copper plating bath is used. Said high concentration copper plating bath comprises copper ions in a concentration of 10 to 70 g/L, preferably of 20 to 50 g/L, and an acid in a concentration of 10 to 400 g/L, preferably of 50 to 200 g/L. This increases the conductivity of the bath resulting in a faster copper deposition.

Method According to the Invention

The steps are preferably carried out in the given order but not necessarily in immediate order. Steps (ii) and optional step (iii) may be carried out at the same time, subsequently or step (ii) is carried out followed by optional step (iii) while step (ii) is continued. It is preferred that the method according to the invention comprises optional step (iii), thus making the metal deposition an electrolytic metal deposition. The method optionally comprises further steps in-between the named steps such as rinsing, drying or pretreatment steps which are known in the art.

Any substrate may be used in the method according to the invention. Typical substrates are conductive and semi-conductive substrates. Conductive substrates are metallic substrates including metallic seed layers as well (e.g. palladium deposited on a typical non-conductive substrate such as plastics to make the latter receptive for metal plating); semi-conductive substrates are exemplarily silicon and glass substrates. The substrate has at least one surface suitable to be treated with the inventive plating bath. The substrates are made in their entirety of the materials listed above or they only comprise one or more surfaces made of the materials listed above. It is also possible within the meaning of the present invention to treat more than one surface simultaneously or subsequently.

Preferably, the substrate is selected from the group consisting of printed circuit boards, IC substrates, circuit carriers, interconnect devices, semiconducting wafers and glass substrates. More preferred are substrates of the afore-mentioned group which have one or more recessed structures such as trenches, blind micro vias, through silicon vias and through glass vias. The metal or metal alloy, preferably copper or copper alloys, are then deposited into the recessed structures.

The plating bath according to the invention is operated from 10 to 100° C. for any time sufficient to deposit the desired deposit thickness. Suitable temperatures and durations can be determined by the person skilled in the art by routine experiments.

The plating bath can be either used in conventional vertical or horizontal plating equipment. Alternatively, fountain plating equipment may be used. The substrate or at least a portion of the surface may be contacted with the inventive plating bath by means of spraying, wiping, dipping, immersing or by other suitable means. Thereby, a metal or metal alloy deposit, preferably a copper or copper alloy deposit, is obtained on at least a portion of the surface of the substrate.

It is preferential to agitate the plating bath or the substrate during the plating process, i.e. the deposition of metal or metal alloy. Agitation may be accomplished for example by mechanical movement of the plating bath like shaking, rotation, stirring; by mechanical movement of the substrate in the plating bath such as rotation thereof or by continuously pumping of the liquids or by ultrasonic treatment, elevated temperatures or gas feeds (such as purging the plating bath with air or an inert gas such as argon or nitrogen).

Optionally, the at least one substrate is subjected to one or more pre-treatment steps. Pre-treatment steps are known in the art. The pre-treatment steps can be for example cleaning steps, (micro-) etching steps and activation steps. Cleaning steps typically use aqueous solutions comprising one or more surfactants and are used to remove contaminants, e.g. from the at least one surface of the substrate which are detrimental to the metal plating deposition. (Micro-) Etching steps usually employ acidic solutions, optionally comprising one or more oxidant such as hydrogen peroxide, to increase the surface area of the at least one surface of the substrate. Activation steps usually require the deposition of a metal catalyst, most often palladium, on the at least one surface of the at least one substrate to render said at least one surface more receptive for metal deposition. Sometimes an activation step is preceded by a pre-dip step or succeeded by a post-dip step, both which are known in the art.

The preferred copper plating bath is preferably operated in the method according to the present invention in a temperature range of 15° C. to 50° C., more preferably in a temperature range of 20° C. to 40° C. by applying an electrical current to the substrate and at least one anode. Preferably, a cathodic current density range of 0.05 A/dm$^2$ to 12 A/dm$^2$, more preferably 0.1 A/dm$^2$ to 7 A/dm$^2$ is applied.

In one embodiment of the present invention which is particularly suitable if a low concentration copper plating bath is used in the method according to the invention is as follows: first a low current density (e.g. 0.5 to 5 mA/cm$^2$) is used for example to fill recessed structures followed by one or more high current density steps wherein each of said steps has a current density higher than that of the first low current density step which is useful for the overburden stage (see also the method disclosed in US 2014/209476 A1, in particular paragraphs 69-74 and FIG. 7 thereof). E.g. the current density in the one or more high current density steps ranges preferably 10 to 20 or 30 mA/cm$^2$. Optionally, the low current density step is preceded by a hot entry step which employs a high current density for a very short period of time, e.g. 15 to 20 mA/cm$^2$ for 0.05 to 1 s.

If optional step (iii) is included in the method according to the invention, the inventive plating bath plating bath can be used for DC plating and (reverse) pulse plating. Both inert and soluble anodes can be utilized when depositing the metal or metal alloy from the plating bath according to the present invention.

It is an advantage of the present invention that the copper plating bath allows for uniformal filling of recessed structures and that the deposits are free of voids and dimples. Uniformal filling is to be understood in the context of the present invention that different recessed structures having different aspect ratios such as trenches which generally have an aspect ratio of <1 and vias generally which have an aspect ratio of >1 can be filled in one step resulting in similar layer distribution in these different recessed structures having different aspect ratios.

It is a further advantage of the present invention that the copper plating bath allows for optimal mounding results to be obtained. Mounding means that a planar copper deposit can be obtained that does neither show any dimples nor any overburdens.

Preferably, pure copper is deposited (disregarding any trace impurities commonly present in technical raw materials). Pure copper is particularly useful in the semiconductor industry due to its high conductivity. Pure copper shall be understood in the context of the present invention that a minimum copper content of 95 wt.-% based on the entire metal content of a deposit is formed, preferably 98 wt.-%, more preferably 99.0 wt.-%, most preferably 99.90 wt.-%. In a more preferred embodiment, the deposits formed consist of at least 95 wt.-% copper, preferably at least of 99 wt.-% copper, more preferably at least of 99.9 wt.-% copper.

Advantageously and preferably, the use of the inventive copper plating bath and the method according to the invention allow for copper deposits to be formed which contain less than 1000 mg of organic impurities per kilogram of copper deposit, more advantageously and more preferably, less than 800 mg of organic impurities per kilogram of copper deposit, even more advantageously and even more preferably, less than 600 mg of organic impurities per kilogram of copper deposit, yet even more preferably, less than 200 mg of organic impurities per kilogram of copper deposit and most preferably, less than 100 mg of organic impurities per kilogram of copper deposit.

Use Claim

The present invention further concerns the use of the at least one pyridinium compound in a metal or metal alloy plating bath, particularly as leveler in a copper plating bath.

Above described preferred embodiments apply to this embodiment mutatis mutandis.

The invention will now be illustrated by reference to the following non-limiting examples.

Examples

Commercial products were used as described in the technical datasheet available on the date of filing of this specification unless stated otherwise hereinafter.

$^1$H-NMR spectra were recorded at 400 MHz with a spectrum offset of 4300 Hz, a sweep width of 9542 Hz at 25° C. (NMR spectroscope provided by Bruker Corp.). The solvent used was $d^6$-DMSO unless stated otherwise.

The weight average molecular mass $M_w$ of the pyridinium compounds was determined by gel permeation chromatography (GPC) using the following GPC apparatus and conditions: SECurity GPC System PSS, pump: Agilent 1260, column: PL Aquagel OH 30+40, 40° C., Eluent A: 60 vol.-% 0.3 mol/L with formic acid in water+40 vol.-% methanol, flow: 1 mL/min, detector RI 40° C., time: 30 minutes, injection volume: 50 microliter, calibration: PVP=Poly-(2vinylpyridin), calibration: 800-256000) PPS standards, data system: WIN GPC V8.0.

A FEI Helios Nanolab 450S was used as Focused Ion Beam-Scanning Electron Microscopy (FIB-SEM). Focused Ion Beam milling was used to generate high quality cross sections and high resolution scanning electron microscopy was used for imaging (back scattering, magnification of e.g. 50,000). Deposit thicknesses were obtained using this method.

Alternatively, the deposit thickness was measured at 10 positions of each substrate and was used to determine the layer thickness by XRF using the XRF instrument Fischerscope XDV-SDD (Helmut Fischer GmbH, Germany). By assuming a layered structure of the deposit, the layer thickness can be calculated from such XRF data.

A magnetic sector secondary ion mass spectrometer (MS-SIMS) provided by Cameca SAS was employed, which is a form of Dynamic-SIMS (D-SIMS). A cesium ($Cs^+$) ion beam was used for the analysis of non-metallic impurities including carbon, sulfur, oxygen and chlorine. To calibrate the system, a standard created by ion implantation was used.

A Laser Scanning Confocal Microscope from Olympus (Olympus Lext OLS4100) was used to measure the overburden conformity of plated samples.

The concentrations of the pyridinium compounds in the all the Application Examples are based on the pyridinium compounds themselves, not on the solutions obtained by below-described synthetic methods.

Preparation of 1,3-bis(pyridin-4-ylmethyl)urea (a Starting Material According to Formula (M1))

A 100 ml glass reactor equipped with magnetic stirring bar, condenser, thermometer and bubbler was charged with 12.52 g urea and 46.00 g 4-(aminomethyl)pyridin at room temperature. The reaction mixture was heated to 120° C. within 10 minutes resulting in a minor ammonia formation. The temperature of the reaction mixture was then stepwise increased to 160° C. (19 h at 130° C., 3 h at 140° C., 2 h at 150° C., 19 h at 160° C.). After completion of the reaction, the reaction mixture was cooled to 60° C. and kept there for 4 h prior to cooling it to room temperature. Then, 60 ml ethyl acetate was added, the resulting suspension was stirred for 24 h at 75° C. After cooling to room temperature, the solid was filtered off, washed three times with 50 ml ethyl acetate each and dried in vacuo. 48.81 g (97.6% yield) of a clear, white solid were obtained. $^1$H-NMR (DMSO): δ=4.26 (4H), 6.75 (2H), 7.25 (4H), 8.49 (4H).

Preparation of 1,3-bis(pyridin-3-ylmethyl)urea (a Starting Material According to Formula (M1))

Above described preparation method was repeated with 12.52 g urea and 45.10 g 3-(aminomethyl)pyridin. 47.21 g (94.4% yield) of a clear, white solid were obtained. $^1$H-NMR (DMSO): δ=4.26 (4H), 6.62 (2H), 7.35 (2H), 7.65 (2H), 8.45 (4H).

Preparation of 1,3-bis(pyridin-2-ylmethyl)urea (a Starting Material According to Formula (M1))

Above described preparation method was repeated with 12.52 g urea and 45.10 g 2-(aminomethyl)pyridin. 47.82 g (95.6% yield) of a clear, white solid were obtained. $^1$H-NMR (DMSO): δ=4.31 (4H), 6.72 (2H), 7.25 (4H), 7.75 (2H), 8.50 (2H).

Preparation of Pyridinium Compound 1 (PC1)

A 100 ml glass reactor equipped with magnetic stirring bar, condenser and temperature sensor was charged with 12.67 g 1,3-bis(pyridin-4-ylmethyl)urea (a starting material according to formula (M1)) and 30 g water prior to heating to 80° C. Then, 7.48 g 1,2-bis(2-chloroethoxy)ethane (a compound (B3)) was added dropwise and the resulting mixture was stirred for 26 h while monitoring the pH value. Once the reaction was completed as indicated by a constant pH value, a clear auburn solution was obtained which was further diluted with water to give 50 g of a 40 wt.-% solution of pyridinium compound 1 in water.

$M_w$ 4600 g/mol, polydispersity 3.7, $^1$H-NMR ($D_2O$): δ=3.48-3.78H (m; 17H), 3.91-4.10 (m; 13H), 4.35-4.46 (m; 5H), 4.51-4.79 (m; 24H), 7.38-7.40 (m; 5H), 7.93-8.01 (m; 12H), 8.46 8.48 (m; 5H), 8.71-8.80 (m; 12H).

Preparation of Pyridinium Compound 2 (PC2)

A 100 ml glass reactor equipped with magnetic stirring bar, condenser and temperature sensor was charged with 12.67 g 1,3-bis(pyridin-3-ylmethyl)urea (a starting material according to formula (M1)) and 30 g water prior to heating to 80° C. Then, 7.48 g 1,2-bis(2-chloroethoxy)ethane (a compound (B3)) was added dropwise and the resulting mixture was stirred for 55 h while monitoring the pH value. Once the reaction was completed as indicated by a constant pH value, a clear yellow solution was obtained which was further diluted with water to give 50 g of a 40 wt.-% solution of pyridinium compound 2 in water.

$M_w$ 2300 g/mot, polydispersity 2.3, $^1$H-NMR ($D_2O$): δ=3.50-3.78 (m; 14H), 3.88-4.10 (m; 12H), 4.33-4.41 (m; 4H), 4.49-4.58 (m; 12H), 4.37-4.54 (m; 2H), 7.74-7.83 (m; 2H), 7.96-8.10 (m; 6H), 8.39-8.57 (m; 10H), 8.65-8.78 (m; 13H)

Preparation of Pyridinium Compound 3 (PC3)

A 100 ml glass reactor equipped with magnetic stirring bar, condenser and temperature sensor was charged with 12.67 g 1,3-bis(pyridin-2-ylmethyl)urea (a starting material according to formula (M1)) and 30 g water prior to heating to 80° C. Then, 7.48 g 1,2-bis(2-chloroethoxy)ethane (a compound (B3)) was added dropwise and the resulting mixture was stirred for 78 h giving an auburn solid after reaching a constant pH value. The product was then dissolved in water to give 50 g of a 40 wt.-% solution of pyridinium compound 3 in water.

$M_w$<880 g/mol, $^1$H-NMR ($D_2O$): δ=3.49-3.80 (m; 21H), 3.81-3.89 (m; 2H), 3.90-4.12 (m; 5H), 4.42-4.52 (m; 9H), 4.63-4.79 (m; 3H), 4.82-4.95 (m; 7H), 7.30-7.54 (m; 10H), 7.81-8.15 (m; 10H), 8.40-8.89 (m; 10H).

Application Example 1: Control of Overburden Uniformity (Mounding Properties)

A solution comprising 5 g/L $Cu^{2+}$ ions (added as copper sulfate), 10 g/L sulfuric acid, 50 mg/L chloride ions (added as hydrochloric acid), 4 mL/L Atomplate® suppressor and 4.3 mL/L Atomplate® accelerator (both products of Atotech Deutschland GmbH) was used. The pyridinium compounds were added as leveler to said solution in concentration as given in the subsequent table to give the individual copper plating baths.

Substrates consisting of coupons of approximately 20 mm×25 mm cleaved from a 300 mm 32 nm node test pattern wafer using low-k dielectric. ALL features were 200 nm deep. Features used for these experiments had a line to space ratio of 1:1 and had a pitch of 100 nm. The barrier/Liner/seed stack consisted of 3 nm TaN/3 nm Ta/30 nm Cu using industry standard PVD methods on an AMAT Endura tool. The coupons were plating in a beaker-scale coupon plating apparatus where the temperature was 25° C., and the anode was soluble copper separated by a nafion membrane from cathode chamber. The waveform consisted of an entry step followed by three distinct plating steps. The entry step used a potential controlled hot entry to match a nominal 16 mA/cm$^2$ at 90 RPM for 0.1 s. The first plating step was 4 mA/cm$^2$ at 30 RPM for 24 s. The second plating step was at 10 mA/cm$^2$ at 30 RPM for 14 s. The third plating step was at 20 mA/cm$^2$ at 150 RPM for 40 s. The final thickness of the film was approximately 400 nm.

After plating, an area of dense 1:1 line arrays of 100 nm pitch of approximately 50 μm long and 100 um wide was selected to assess the mounding properties (i.e. the presence of an overburden or a dimple) and was analysed with a confocal microscope. The results are summarised in Table 1.

TABLE 1

Mounding results

| # | | concentration | PC1 [nm] | PC2 [nm] | PC3 [nm] |
|---|---|---|---|---|---|
| 1 | comparative example | 0 mg/L | 590 ± 20 | 590 ± 20 | 590 ± 20 |
| 2 | inventive example | 1 mg/L | 168 | 243 | 455 |
| 3 | inventive example | 2 mg/L | 121 | 36 | 350 |
| 4 | inventive example | 3.5 mg/L | 35 | 20 | 276 |
| 5 | inventive example | 5 mg/L | −2 | −7 | 187 |
| 6 | inventive example | 10 mg/L | −21 | | 114 |

All the pyridinium compound showed a levelling effect which improved with increasing concentration. Surprisingly, it was found that the levelling effect of PC1 and PC2 is much more pronounced compared to that of PC3. Thus, copper plating baths can be easily obtained which do not give undesired overburdens or dimples when depositing copper into recessed structures.

Application Example 2: Filling Performance

A solution comprising 5 g/L $Cu^{2+}$ ions (added as copper sulfate), 10 g/L sulfuric acid, 50 mg/L chloride ions (added as hydrochloric acid), 4 mL/L Atomplate® suppressor, 4.3 mL/L Atomplate® accelerator (both products of Atotech Deutschland GmbH) and 3.5 mL/L of pyridinium compound PC1 was used.

A substrate consisting of coupons of approximately 20 mm×25 mm cleaved from a 300 mm 32 nm node test pattern wafer using low-k dielectric was used. ALL features were 200 nm deep. Features used for these experiments had a line to space ratio of 1:1 and had a pitch of 48 nm. The barrier/Liner/seed stack consisted of 3 nm TaN/3 nm Ta/30 nm Cu using industry standard PVD methods on an AMAT Endura tool. The coupons were plating in a beaker-scale coupon plating apparatus where the temperature was 25° C., and the anode was soluble copper separated by a nafion membrane from cathode chamber. The waveform consisted of an entry step followed by three distinct plating steps. The entry step used a potential controlled hot entry to match a nominal 16 mA/cm$^2$ at 90 RPM for 0.1 s. The first plating step was 4 mA/cm$^2$ at 30 RPM for 24 s. The second plating step was at 10 mA/cm$^2$ at 30 RPM for 14 s. The third plating step was at 20 mA/cm$^2$ at 150 RPM for 40 s. The final thickness of the film was approximately 400 nm.

Figure 1:
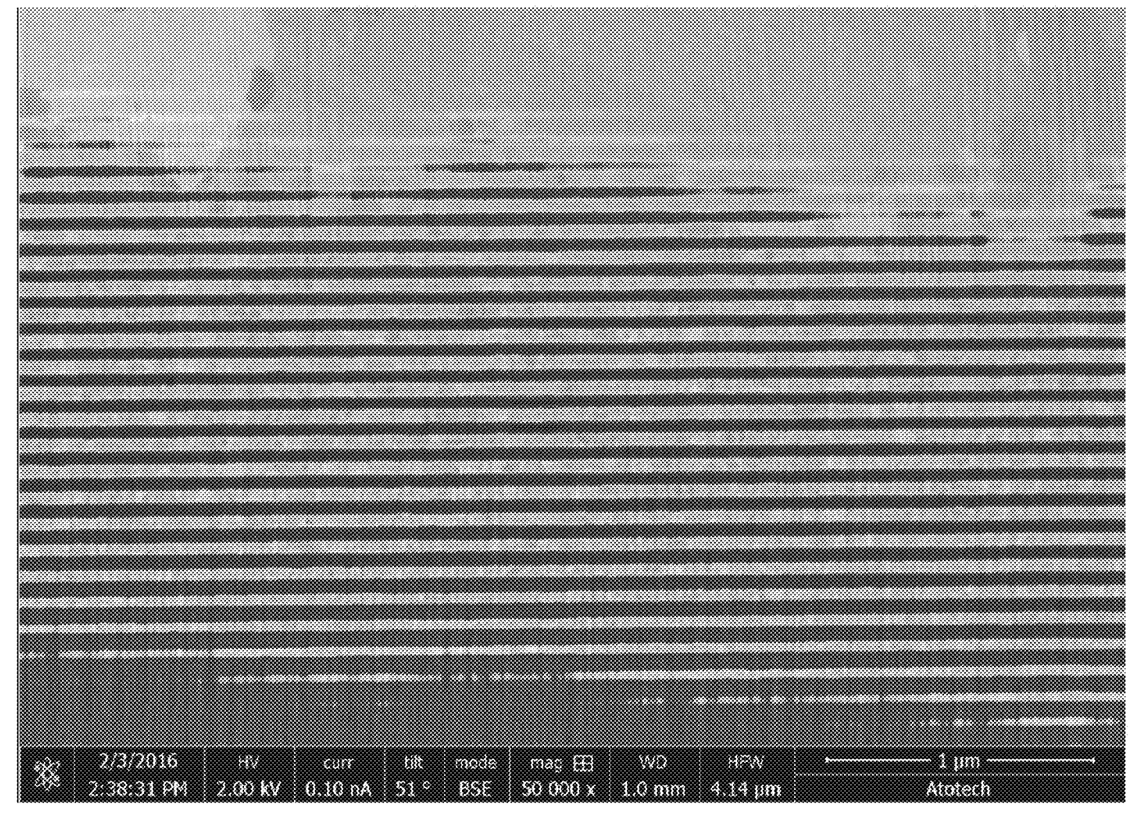
FIG. 1 shows a planar cross section of a wafer substrate treated with a copper plating bath according to the invention (Application Example 2). The copper deposit is free of voids as required by today's industry standards.

After plating, an area of dense 1:1 Line arrays of 100 nm pitch of approximately 50 μm long and 100 μm wide was inspected with FIB-SEM cross-section images. This can be seen in FIG. 1 which shows a planar cross section of a substrate. The cross section was prepared by cutting the plated substrate at a certain angle to make the individual copper lines at various depths visible. The substrate was completely filled and the copper deposits were free of voids.

Application Example 3: Defects in Copper Deposits (SP2 and SP3 Defects)

As substrates, 300 mm unpatterned wafers with uniform layers as follows were used. The dielectric layer was 100 nm $SiO_2$ formed from tetraethoxysilane. The barrier/liner/seed stack consisted of 4 nm TaN/2 nm Ta/45 nm Cu using industry standard PVD methods on an AMAT Endura tool. The wafers were plated in a Sabre® Extreme™ plating tool (LAM Research). The substrates were contacted in said plating tool with a copper plating baths each comprising 5 g/L $Cu^{2+}$ ions (added as copper sulfate), 10 g/L sulfuric acid, 50 mg/L chloride ions (added as sodium chloride), 4 mL/L Atomplate® suppressor, 4 mL/L Atomplate® accelerator (both products of Atotech Deutschland GmbH) and pyridinium compound PC1 in concentrations as given in the subsequent table where the temperature was 25° C. The waveform consisted of an entry step followed by three distinct plating steps. The entry step used a potential controlled hot entry to match a nominal 16 mA/cm$^2$ at 90 RPM for 0.1 s. The first plating step was 4 mA/cm$^2$ at 30 RPM for 24 s. The second plating step was at 10 mA/cm$^2$ at 30 RPM for 14 s. The third plating step was at 20 mA/cm$^2$ at 150 RPM for 80 s. The final thickness of the film was approximately 700 nm. Then, the substrates with the copper deposit formed thereon were analyzed using both a KLA Tencor Surfscan SP2 and a KLA Tencor Surfscan SP3 (KLA Tencor Corporation) to count the defects formed in the copper deposit. The results are summarized in Table 2.

TABLE 2

Number of defects in copper deposits in dependence on the concentration of the pyridinium compound in a copper plating bath.

| # | | Concentration of PC1 [mg/L] | Number of SP2 defects | Number of SP3 defects |
|---|---|---|---|---|
| 1 | comparative example | 0 | >10,000 | >10,000 |
| 2 | inventive example | 2 | 34 | 88 |
| 3 | inventive example | 3.5 | 61 | 40 |
| 4 | inventive example | 5 | 12 | 47 |

The copper deposits formed with the inventive copper plating baths comprising the inventive pyridinium compounds had very little defects. Few defects are highly desired in the semiconductor industry as this e.g. facilitates optical inspections of such obtained copper deposits and increases the overall yield.

Comparative Example 1: Defects in Copper Deposits (SP2 and SP3 Defects)

Application Example 3 was repeated but instead of the inventive pyridinium compound, polyethylenimine ($M_w$: 2000 g/mol) was used in a concentration of 2 mg/L. The number of SP2 and SP3 defects was over 10,000 for both measurements.

Thus, the number of defects in a copper deposit can be significantly reduced when using the inventive pyridinium compounds as levelers in a copper plating bath.

Application Example 4: Copper Deposit Purity

As substrates, 300 mm unpatterned wafers with uniform layers were used. The dielectric layer was 100 nm $SiO_2$ formed from tetraethoxysilane. The barrier/liner/seed stack consisted of 4 nm TaN/2 nm Ta/45 nm Cu using industry standard PVD methods on an AMAT Endura tool. The wafers were plated in a Sabre® Extreme™ plating tool (LAM Research). The substrates were contacted in said plating tool with a copper plating baths each comprising 5 g/L $Cu^{2+}$ ions (added as copper sulfate), 10 g/L sulfuric acid, 50 mg/L chloride ions (added as sodium chloride), 4 mL/L Atomplate® suppressor, 4 mL/L Atomplate® accelerator (both products of Atotech Deutschland GmbH) and additives in concentrations as given in the subsequent table where the temperature was 25° C. The waveform consisted of an entry step followed by three distinct plating steps. The entry step used a potential controlled hot entry to match a nominal 16 mA/cm² at 90 RPM for 0.1 s. The first plating step was 4 mA/cm² at 30 RPM for 24 s. The second plating step was at 10 mA/cm² at 30 RPM for 14 s. The third plating step was at 20 mA/cm² at 150 RPM for 80 s. The final thickness of the film was approximately 700 nm. The formed copper deposits were analyzed by secondary ion mass spectrometry (SIMS). The results are provided in Table 3.

TABLE 3

Organic residues in copper deposits.

| Additives | Carbon [mg/kg] | Oxygen [mg/kg] | Sulfur [mg/kg] | Chlorine [mg/kg] |
|---|---|---|---|---|
| No leveler[1] | 33.9 | 20.8 | 0.6 | 0.2 |
| 2 mg/L polyethylene imine[1] | 166.9 | 85.1 | 103.1 | 88.6 |
| 3.5 mg/L PC1[2] | 2.31 | 3.15 | 0.18 | 0.15 |

[1]comparative example;
[2]inventive example

The amounts of carbon, sulfur, chlorine and oxygen present in the copper deposits have been measured. These atoms results from organic or polymeric impurities to be present in the copper deposits. It can be seen that the copper deposits formed in the comparative example all exhibited significantly higher amounts of such organic impurities. In contrast to that, the inventive pyridinium compounds in copper plating baths allowed for very little organic impurities to be built into the copper deposits.

Other embodiments of the present invention will be apparent to those skilled in the art from a consideration of this specification or practice of the invention disclosed herein. It is intended that the specification and examples be considered as exemplary only, with the true scope of the invention being defined by the following claims only.

The invention claimed is:

1. A compound comprising a building block according to formula (I)

(I)

wherein each A represents a unit independently selected from the following formulae (A1) and (A2)

(A1)

(A2)

wherein $R^{a1}$, $R^{a2}$, $R^{a3}$ and $R^{a5}$ are each selected independently from the group consisting of C1-C12-alkanediyl and —(CH$_2$)$_c$—[CH(R$^{a6}$)—CH$_2$—O]$_d$—(CH$_2$)$_e$—
wherein c is an integer ranging from 0 to 3; d is an integer ranging from 1 to 100; e is an integer ranging from 1 to 3;

each $R^{a6}$ is independently from each other selected from the group consisting of hydrogen, alkyl, aryl and aralkyl;

each $R^{a4}$ is independently selected from the group consisting of alkanediyl, arenediyl and —(CH$_2$)$_f$—[CH(R$^{a7}$)—CH$_2$—O]$_g$—(CH$_2$)$_h$—, wherein f is an integer ranging from 0 to 3; g is an integer ranging from 1 to 100; h is an integer ranging from 1 to 3; each $R^{a7}$ is independently from each other selected from the group consisting of hydrogen, alkyl, aryl and aralkyl;

each $X^1$ and $X^2$ are independently selected from the group consisting of

-continued wherein Z is selected from —CH$_2$—, O, S; z and z' are integers independently ranging from 1 to 6, each R$^{a8}$ and R$^{a9}$ are independently selected from the group consisting of hydrogen, alkyl, aryl, aralkyl and —CH$_2$—CH$_2$—(OCH$_2$CH$_2$)$_y$—OH wherein y is an integer from 1 to 4;

each Y$^1$, Y$^2$ and Y$^3$ are independently selected from the group consisting of O and) N(R$^{a10}$) wherein each R$^{a10}$ is independently selected from the group consisting of hydrogen, alkyl, aryl and aralkyl;

a is an integer ranging from 1 to 40; and each D is independently selected from the group consisting of —CH$_2$—CH(OH)—CH$_2$—, —CH$_2$—CH(SH)—CH$_2$—, —(CH$_2$)$_i$—[CH(R$^{d1}$)—CH$_2$—O]$_j$—(CH$_2$)$_k$— and —CH$_2$—CH(OH)—(CH$_2$)$_l$—[CH(R$^{d2}$)—CH$_2$—O]$_m$—(CH$_2$)$_n$—CH(OH)—CH$^2$— wherein i is an integer ranging from 0 to 3; j is an integer ranging from 1 to 100; k is an integer ranging from 1 to 3; each R$^{d1}$ is independently from each other selected from the group consisting of hydrogen, alkyl, aryl and aralkyl; l is an integer ranging from 1 to 3; m is an integer ranging from 1 to 100; n is an integer ranging from 1 to 3; each R$^{d2}$ is independently from each other selected from the group consisting of hydrogen, alkyl, aryl and aralkyl.

2. The compound according to claim 1 wherein each R$^{a1}$, R$^{a2}$, R$^{a3}$ and R$^{a5}$ are independently selected from 1,1-methylene (—CH$_2$—), 1,2-ethylene (—CH$_2$—CH$_2$—), 1,3-propylene (—CH$_2$—CH$_2$—CH$_2$—), —(CH$_2$)$_2$—O—(CH$_2$)$_2$— and —(CH$_2$)$_2$—O—(CH$_2$)$_2$—O—(CH$_2$)$_2$—.

3. The compound according to claim 1 wherein X$^1$ and X$^2$ are

4. The compound according to claim 1 wherein each D is —(CH$_2$)$_i$—[CH(R$^{d1}$)—CH$_2$—O]$_j$—(CH$_2$)$_k$— wherein each i is 2 or 3; each j is an integer ranging from 1 to 25, each k is an integer ranging from 2 to 3 and each R$^{d1}$ is independently selected from the group consisting of hydrogen and C1-C4-alkyl.

5. The compound according to claim 1 wherein R$^{a1}$ to R$^{a5}$ are free of nitrogen atoms.

6. The compound according to claim 3 wherein at least one A is selected to be a unit represented by formula (A1-1) or (A1-2)

7. The compound according to claim 6 wherein all A are selected to be a unit represented by formula (A1-1) or (A1-2)

8. The compound according to claim 1 wherein its weight average molecular mass M$_w$ ranges from 250 to 10000 g/mol.

9. A method of synthesizing a compound claim 1 characterized in that at least one starting material represented by one of the following formulae (M1) and M2)

wherein
R$^{m1}$, R$^{m2}$, R$^{m3}$ and R$^{m5}$ are each selected independently from the group consisting of C1-C12-alkanediyl and —(CH$_2$)$_\alpha$—[CH(R$^{m6}$)—CH$_2$—O]$_\beta$—(CH$_2$)$_X$— wherein α is an integer ranging from 0 to 3; β is an integer ranging from 1 to 100; X is an integer ranging from 1 to 3; each R$^{m6}$ is independently from each other selected from the group consisting of hydrogen, alkyl, aryl and aralkyl;

each R$^{m4}$ is independently selected from the group consisting of alkanediyl, arenediyl and —(CH$_2$)$_\delta$—[CH(R$^{m7}$)—CH$_2$—O]$_\varepsilon$—(CH$_2$)$_\phi$—, wherein δ is an integer ranging from 0 to 3; ε is an integer ranging from 1 to 100; φ is an integer ranging from 1 to 3; each R$^{m7}$ is independently from each other selected from the group consisting of hydrogen, alkyl, aryl and aralkyl;

each of $M^1$, $M^3$ and $M^4$ is independently selected from the group consisting of O and $N(R^{m10})$ wherein each $R^{m10}$ is independently selected from the group consisting of hydrogen, alkyl, aryl and aralkyl; and each of $M^2$ and $M^5$ is independently selected from the group consisting of wherein Z is selected from —CH$_2$—, O, $\zeta$ and $\zeta'$ are integers independently ranging from 1 to 6, each $R^{m8}$ and $R^{m9}$ are independently selected from the group consisting of hydrogen, alkyl, aryl, aralkyl and —CH$_2$—CH$_2$—(OCH$_2$CH$_2$)$_\psi$—OH wherein $\psi$ is an integer from 1 to 4 is reacted with one or more of the following compounds (B1) to (B4)

(B1)

(B2)

(B3)

and (B4)

wherein each LG is independently selected from the group consisting of triflate, nonaflate, alkylsulfonates, arylsulfonates and halides;

$\iota$ is an integer ranging from 0 to 3; $\varphi$ is an integer ranging from 1 to 100; $\kappa$ is an integer ranging from 1 to 3; each $R^{n1}$ is independently from each other selected from the group consisting of hydrogen, alkyl, aryl and aralkyl; $\lambda$ is an integer ranging from 1 to 3; $\mu$ is an integer ranging from 1 to 100; $\nu$ is an integer ranging from 1 to 3; each $R^{n2}$ is independently from each other selected from the group consisting of hydrogen, alkyl, aryl and aralkyl.

10. A metal or metal alloy plating bath comprising at least one type of reducible metal ions characterized in that said metal or metal alloy plating bath comprises at least one compound according to claim 1.

11. The metal or metal alloy plating bath according to claim 10 wherein the at least one type of reducible metal ions are copper ions.

12. The metal or metal alloy plating bath according to claim 11 wherein the concentration of the at least one compound in the metal or metal alloy plating bath ranges from 0.01 mg/L to 1000 mg/L.

13. A method for deposition of metal or metal alloy onto at least one surface of a substrate comprising the steps
  (i) providing a substrate,
  (ii) contacting the surface of the substrate with an aqueous metal or metal alloy plating bath according to claim 10, and
  (iii) optionally, applying an electrical current between the substrate and at least one anode,
  and thereby depositing a metal or metal alloy on at least a portion of the surface of a substrate.

14. The method of claim 13 wherein the substrate is selected from the group consisting of printed circuit boards, IC substrates, circuit carriers, interconnect devices, semiconducting wafers and glass substrates.

15. The method of claim 13 wherein the metal or metal alloy is copper or a copper alloy.

* * * * *